United States Patent
Nakamura et al.

[11] Patent Number: 6,057,471
[45] Date of Patent: *May 2, 2000

[54] AMMOXIDATION METHOD IN FLUIDIZED-BED REACTOR

[75] Inventors: Toshio Nakamura, Yokohama; Hiroshi Murata, Otake; Katsumasa Nishijima, Yokohama; Masanori Yamaguchi, Yokohama; Yoshikazu Sawada, Yokohama, all of Japan

[73] Assignee: Mitsubishi Rayon Co., Ltd., Tokyo-To, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/936,911

[22] Filed: Sep. 25, 1997

[30] Foreign Application Priority Data

Sep. 25, 1996 [JP] Japan ..................................... 8-253491
Jul. 22, 1997 [JP] Japan ..................................... 9-210220
Aug. 1, 1997 [JP] Japan ..................................... 9-207637

[51] Int. Cl.[7] ..................... C07C 253/18; C07C 253/26; C07C 253/28; C07C 253/34
[52] U.S. Cl. ......................... 558/321; 558/322; 558/323; 558/324; 558/327
[58] Field of Search ................................... 558/322, 323, 558/324, 327, 321

[56] References Cited

U.S. PATENT DOCUMENTS 3,988,359  10/1976  Saito et al. .
4,083,804  4/1978  Saito et al. ............................. 252/432
4,102,914  7/1978  Beuther et al. ...................... 260/465.3
4,511,548  4/1985  Attig et al. ............................. 423/376
4,801,731  1/1989  Jordan .
5,158,787  10/1992  Sasaki et al. ........................... 423/376

FOREIGN PATENT DOCUMENTS 0340909  11/1989  European Pat. Off. .
0446379  9/1991  European Pat. Off. .
96/23582  8/1996  WIPO .
96/31465  10/1996  WIPO .

*Primary Examiner*—Johann Richter
*Assistant Examiner*—Taofiq A. Solola
*Attorney, Agent, or Firm*—Wenderoth, Lind & Ponack, L.L.P.

[57] ABSTRACT

An ammoxidation method in a fluidized-bed reactor, in which, when a starting material to be ammoxidized is ammoxidized by means of vapor-phase catalytic fluidized-bed reaction, the reaction is carried out in a fluidized-bed reactor to which an oxygen-containing gas is fed through feed openings provided at the bottom thereof, and a starting material to be ammoxidized is fed through feed openings provided above the feed openings for the oxygen-containing gas, the distance between the feed openings for the oxygen-containing gas and those for the starting material being from 30 to 250% of the height of a fluidized solid matter in a static state so as to form such a fluidized bed that the density of the fluidized solid matter at the feed openings for the starting material to be ammoxidized is in the range of 50 to 300 kg/m$^3$ and that the gas velocity is 1 m/s or lower. By this method, the efficiency of contact between catalyst particles and a starting material, and the result of the reaction (the yield of a desired product) are improved.

17 Claims, 1 Drawing Sheet

AMMOXIDATION METHOD IN FLUIDIZED-BED REACTOR

BACKGROUND OF THE INVENTION

1. Field of the Invention

The present invention relates to a method for carrying out vapor-phase catalytic ammoxidation in a fluidized-bed reactor, and provides an economically advantageous method for producing, from a starting material to be ammoxidized (hereinafter referred to as a starting hydrocarbon or the like), a corresponding nitrile in an increased yield.

2. Related Art

Ammoxidation in which a hydrocarbon or the like is brought into contact with ammonia and oxygen in the presence of a catalyst to produce a nitrile by one reaction step is very useful from the industrial point of view. It is well known that, when methanol is used as the starting hydrocarbon or the like, hydrocyanic acid is produced (therefore, in the present invention, "starting materials to be ammoxidized" are not limited to hydrocarbons, and "nitriles" also include HCN); and that, when propylene, isobutylene or 2,6-dichlorotoluene is used, acrylonitrile, methacrylonitrile or 2,6-dichlorobenzo-nitrile is produced, respectively. These nitriles are used in large quantities as starting materials for polymeric compounds such as resins and fibers, and for a variety of chemicals.

In general, the optimum temperature range for carrying out the ammoxidation reaction of such a hydrocarbon or the like is narrow, and, in addition, the amount of exothermic energy generated by the reaction is large. Therefore, a fluidized-bed reactor is often used for this ammoxidation reaction because it is excellent in temperature controllability and because it can treat a high-concentration starting gas, and thus can attain high productivity. However, in a conventional fluidized-bed reactor, a starting gas to be fed to the reactor passes through a catalyst bed as a large number of bubbles, so that contact between the starting gas and the catalyst tends to be insufficient. On the other hand, a fluidized-bed catalyst is characterized in that the mixing of the catalyst particles, including the mixing of the catalyst particles in an upward stream with those in a downward stream can be successfully attained. However, due to this characteristic feature, the mixing of an upward gas stream with a downward gas stream, that is, back mixing tends to occur in the catalyst bed.

For the above-described reasons, when a conventional fluidized-bed reactor is used, the yield of a nitrile tends to be low, as compared with a case where a fixed-bed reactor is used. In order to solve this problem residing in fluidized-bed reaction, many proposals have been made so far. These proposals can be classified broadly into the following three types of methods.

Methods classified in the first group are such that shaped articles made out of wire-netting, screens, grids, perforated plates, horizontal plates, vertical pipes or the like are laid in a catalyst bed as obstacles to prevent the coalescence or growth of bubbles so as to promote the division of the bubbles, or to control the state of the mixing of the catalyst particles, thereby improving contact between the starting gas and the catalyst (the methods described in, for example, Japanese Patent Publications No. 2533/1965, No. 28491/1969, No. 531/1973 and No. 38428/1983 (the specification of U.S. Pat. No. 4,082,786), the specification of U.S. Pat. No. 3,783,528, etc.). In these methods, it seems that contact between a starting gas and a catalyst is improved when the obstacles are laid densely. However, such obstacles are not practical because the construction for laying them is complicated. Moreover, they excessively prevent the mixing of catalyst particles, so that the characteristics of the fluidized bed such that e.g., the temperature controllability is excellent, and the temperature of the catalyst bed becomes uniform would not be fully utilized; and, at the same time, the catalyst in the reactor is distributed unevenly in terms of space and time, so that it becomes difficult to carry out the reaction stably and continuously. On the other hand, when the obstacles are laid so that relatively good temperature controllability can be obtained, the contact between the reactant gas and the catalyst would not be fully improved.

Methods classified in the second group are to control the distribution of the concentration of a starting gas in a reactor in order to increase the rate of the utilization of the starting gas in the reaction. In these methods, a starting material is fed through two feed openings separately provided at two different points; or, after a starting hydrocarbon or the like is thoroughly mixed with ammonia and oxygen, the mixture is brought into substantial contact with a catalyst. These methods are described, for instance, in Japanese Patent Publication No. 41369/1970 (the specification of U.S. Pat. No. 3,546,268), Japanese Patent Laid-Open Publications No. 9751/1982, No. 258/1990 (the specification of U.S. Pat. No. 4,801,731) and No. 157355/1991. However, these methods have been proposed not for improving the efficiency of contact between a reactant gas and a catalyst, which is a fundamental problem confronting fluidized beds, but for improving the state of the mixing of a starting gas. Although the starting gas is maintained, for a short time after the feeding thereof, in a state which can meet the object, these methods would not solve the problem that a catalyst and a starting hydrocarbon or the like cannot be brought into intimate contact due to the growth or enlargement of bubbles generated while the starting gas is passing through the catalyst bed, and would not fully prevent the cause of uneven distribution of residence time due to the back mixing of the gas. These methods are thus unsatisfactory as a means for improving contact between a gas and catalyst particles.

Methods classified in the third group utilize a fluidized state which is essentially different from that in a conventional fluidized bed. These methods are such that a fluidized bed is formed by a large amount of catalyst particles which are transported and accompanied by a high-velocity gas stream. The solid matter density of this fluidized bed is relatively low as compared with that of a conventional fluidized bed, and the flow of the gas and that of the catalyst are similar to piston flow. Incidentally, a fluidized bed in such a state was termed "fast fluidization" by Joseph Yerushalmi et al. ("Industrial and Engineering Chemistry Process Design Development", Vol. 15, No. 1, pp. 47–53 (1976)).

As a technique utilizing this high-velocity fluidized bed, there has been known a method described in Japanese Patent Laid-Open Publication No. 144528/1978 (the specification of U.S. Pat. No. 4,102,914). This method is characterized in that reaction is carried out by using a solid matter density of approximately 16 to 240 $kg/m^3$ and a gas velocity of approximately 1.5 to 7.5 m/s, the solid matter density being low and the gas velocity being high as compared with those in a conventional fluidized bed. However, although this method is advantageous in that the productivity per sectional area of a reactor used is high due to high gas velocity, it seems to have the following problem: in order to obtain a desired nitrile in high yield, an extremely long reaction zone is needed; to attain this, it is necessary to considerably increase the height of the reactor when the reactor is in the shape of vertical cylinder, which is a shape common to conventional reactors, so that the construction cost is increased. In order to avoid this problem, the reactor is formed to have a coil-like shape.

However, in a method using this coil-shaped reactor, since centrifugal force acts on catalyst particles which are passing through the coil, a gas and the catalyst particles are unevenly distributed, and contact between them becomes poor. Thus, the effect of improving the contact between the gas and the catalyst particles tends to be insufficient. Further, another problem residing in this method is as follows: if the catalyst is not separated and removed, in a large amount, from the reaction product immediately after the conversion of the starting hydrocarbon or the like reaches an optimum value, the reaction proceeds excessively, and a nitrile is produced in a decreased yield. Furthermore, a separator such as a cyclone is usually employed in this method as a catalyst separator, and, since the amount of the gas and that of the catalyst are large, the cost required for manufacturing a cyclone which can meet this condition, i.e., a cyclone which is large in size, has high collection efficiency, and hardly abrades or powderizes the catalyst, is high. In addition, in this method, it is, in general, necessary to lay a pipe which is useful for transferring the catalyst to the outside of the reactor system, in order to return the catalyst separated from the gas to the reactor again. Moreover, it is necessary to control the pressure balancing so that the reactant gas will not back-flow in this pipe.

Thus, the method for improving contact between a gas and catalyst particles by utilizing high-speed fluidization has such problems that an increased cost is required for plant construction, that the operation is complicated and that the effect for improving contact between a gas and catalyst particles would not be sufficiently obtained depending upon the type of the installation of the plant.

Therefore, expected effects would not be fully obtained.

SUMMARY OF THE INVENTION

The present invention was accomplished in order to solve the aforementioned problems in the conventional techniques for ammoxidizing a starting hydrocarbon or the like in a fluidized-bed reactor. An object of the present invention is therefore to provide a method for economically producing a desired nitrile in an increased yield by improving contact between a starting gas and catalyst particles without adding any special apparatus to a conventional fluidized-bed reactor.

The present invention was accomplished on the basis of the following fact: high gas velocity and relatively low solid matter concentration are not essential requirements for attaining intimate contact between a gas and catalyst particles, which is a characteristic feature of a fluidized bed of high-speed fluidization, and the state of contact between a gas and catalyst particles can be made extremely good, even when the gas velocity is low, by properly controlling the solid matter concentration in a reaction zone.

Namely, an ammoxidation method according to the present invention, which is practiced in a fluidized-bed reactor, is such that, when a starting material to be ammoxidized is ammoxidized by means of vapor-phase catalytic fluidized-bed reaction, the reaction is carried out in a fluidized-bed reactor to which an oxygen-containing gas is fed through feed openings provided at the bottom thereof, and a starting material to be ammoxidized is fed through feed openings provided above the feed openings for the oxygen-containing gas, the distance between the feed openings for the oxygen-containing gas and those for the starting material being from 30 to 250% of the height of a fluidized solid matter in a static state so as to form such a fluidized bed that the density of the fluidized solid matter (i.e., the catalyst bed density) at the feed openings for the starting material to be ammoxidized is in the range of 50 to 300 kg/m$^3$ and that the gas velocity at the feed openings for the same is 1 m/s or lower.

According to the present invention, the efficiency of contact between a starting material and catalyst particles is extremely high, and, as a result, an extremely improved result (the yield of a desired product) can be obtained from the reaction.

DETAILED DESCRIPTION OF THE INVENTION

The ammoxidation method according to the present invention, which is practiced in a fluidized-bed reactor, is a method as claimed in the accompanying claims. The method can be any purposive one, as long as it can fulfill the required conditions or constitution defined in the claims.

<Reaction in Fluidized Bed>

Figure 1:
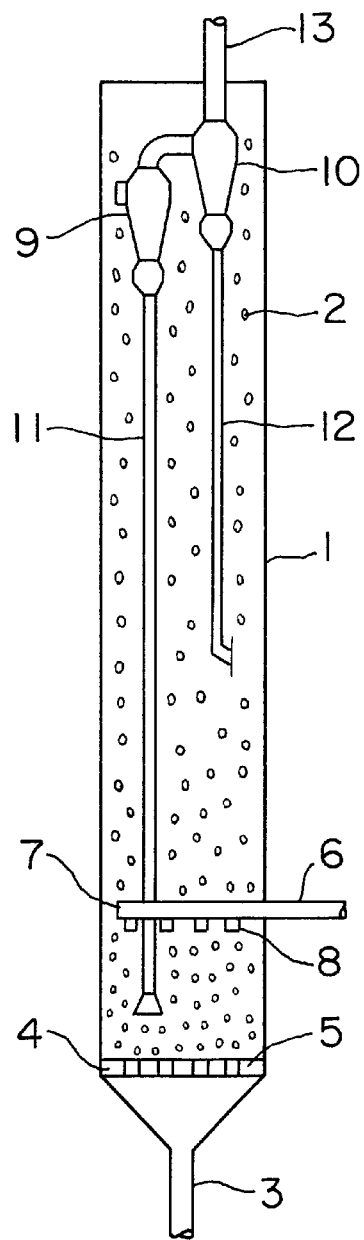
FIG. 1 is a sectional view of one example of the reactor which is used for carrying out generalized ammoxidation in accordance with the method of the present invention, where 1: a reactor, 2: a catalyst, 3: oxygen-containing gas feed pipe, 4,7: a gas-dispersing means, 5,8: openings for the gas dispersing means, 6: a mixture of a starting hydrocarbon or the like and ammonia feed pipe, 9,10: a cyclone separator, 11,12: a pipe for the returning of a catalyst, and 13: an exhaust pipe.

A reactor shown in FIG. 1 can be mentioned as a preferred embodiment of the present invention. As described above, FIG. 1 is only for illustrating one embodiment of the present invention. It is therefore needless to say that the present invention is not limited by the particulars specifically shown in FIG. 1.

A catalyst 2 is housed in a reactor 1. An oxygen-containing gas is introduced into the reactor 1 through a pipe 3, and fed to the lower part of the catalyst bed through openings, viz. feed openings 5 for an oxygen-containing gas, formed in a gas-dispersing means or a gas distributer 4. A starting hydrocarbon or the like and ammonia are introduced into the reactor 1 as a mixture thereof (or separately) through a pipe 6, and fed (in this embodiment and preferably, downward) to the catalyst bed through openings 8, viz. feed openings for a starting hydrocarbon or the like, formed in a gas-dispersing apparatus 7. The feed openings 8 for the starting hydrocarbon or the like are provided above the feed openings for the oxygen-containing gas, the distance between the feed openings for the oxygen-containing gas and those for the starting hydrocarbon or the like being from 30 to 250%, preferably from 50 to 200% of the height of the catalyst bed in a static state, viz. the height of the stationary catalyst bed. At the upper part of the reactor 1 is provided a multicyclone composed of cyclones 9 and 10 arranged in series. The catalyst particles accompanied by the gas stream are separated therefrom by this multicyclone, and returned to the lower or middle part of the catalyst bed through a pipe 11 or 12. With respect to the catalyst particles recovered by the multicyclone, it is preferable that those ones which have smaller particle diameters be returned to the lower part of the catalyst bed. The gas from which the catalyst particles have been removed is allowed to pass through the final cyclone, and exhausted from the reactor 1 through a pipe 13. The oxygen-containing gas which is fed to the bottom of the reactor 1 is, in general, air. However, oxygen-enriched air, or oxygen diluted with an inert gas can also be used instead of air.

As is shown hereinabove, the feed openings for the oxygen-containing gas are means for feeding the oxygen-containing gas to the catalyst bed which is fluidized, and the site of or, when the reactor is vertical, the level or height of the feed openings for the oxygen-containing gas may typically define the bottom of the catalyst fluidized bed.

The starting hydrocarbon or the like for use in the present invention is methanol, propylene, isobutylene, methylbenzene, especially toluene or 2,6-dichlorotoluene, or any other aliphatic hydrocarbon. Hydrocyanic acid is produced from methanol; acrylonitrile is produced from propylene; and methacrylonitrile is produced from isobutylene. All of these compounds are industrially useful chemicals; they are in great demand as starting materials for various derivatives.

It is also possible to feed, to the reactor 1, the above-described starting hydrocarbon or the like in admixture with ammonia and/or an inert gas or steam. As to the feed of steam, reference can be made to the pertinent disclosure in <Ammoxidation of methanol> given hereinbelow.

In the above-described reactor 1, the area between the feed openings 8 for the starting hydrocarbon or the like and the inlet of the cyclone 9 provided at the upper part of the reactor 1 is a main reaction zone. The solid matter density in this reaction zone is from 1 to 300 kg/m$^3$. More specifically, it is important that the density of the fluidized solid matter at the feed openings for the starting hydrocarbon or the like be in the range of 50 to 300 kg/m$^3$, preferably 100 to 250 kg/m$^3$. In general, in order to obtain such a solid matter density, the catalyst particles are made into a state of high-speed fluidization by the use of a high-velocity gas. However, in the present invention, an oxygen-containing gas is fed to the bottom of the catalyst bed as mentioned previously, and feed openings 8 for a hydrocarbon to be fed over the oxygen-containing gas are provided above the feed openings 5 for the oxygen-containing gas, provided that the distance between the feed openings 5 for the oxygen-containing gas and the feed openings 8 for the hydrocarbon being from 30 to 250% of the height of the stationary catalyst bed. By this, the state of contact between the gas and the catalyst can be maintained excellent even when the gas velocity is as low as 1 m/s or lower. The density of the fluidized solid matter, that is, the catalyst bed density, can be determined by obtaining the difference between static pressures measured at two different points on the fluidized bed in the direction of the height thereof, and dividing the difference by the distance between the two points. Therefore, the density of the fluidized solid matter at the feed openings for the starting hydrocarbon or the like can be estimated from the distribution of the density in the direction of the height of the fluidized bed.

The optimum position of the feeding of the starting hydrocarbon or the like varies within the above-described range depending upon the physical properties of the catalyst such as particle diameter, density, etc., the catalytic activity, and the gas velocity. When the position of the feeding of the starting hydrocarbon or the like is lower than 30% of the height of the stationary catalyst bed, the density of the solid matter may be excessively high. Therefore, it may not be easy to make the density at the feed openings for the starting hydrocarbon or the like to approximately 50 to 300 kg/m$^3$ unless the gas velocity is made extremely high. On the other hand, when the position of the feeding of the starting hydrocarbon or the like is higher than 250% of the height of the stationary catalyst bed, the density of the solid matter at the feed openings for the starting hydrocarbon or the like may be approximately 50 to 300 kg/m$^3$. In this case, however, the length of the reaction zone is not sufficiently long, so that it may be impossible to make the conversion of the hydrocarbon or the like sufficiently high.

<Catalyst>

The catalyst for use in the present invention is desirably a highly active one. However, there is no particular limitation on the catalyst, and any known ammoxidation catalyst can be used.

In the present invention, catalysts such as for instance, those containing iron and antimony, and at least one element selected from the group consisting of boron, magnesium, phosphorus, potassium, titanium, vanadium, chromium, manganese, cobalt, nickel, copper, zinc, molybdenum, tin, tellurium, tungsten and bismuth can be used. Specifically, a catalyst represented by the following empirical formula (A) can be used and preferable also:

$$Fe_aSb_bQ_cR_dO_e \tag{A}$$

wherein Q represents at least one element selected from the group consisting of V, Co, Ni, Cu, Mo, W and Bi; R represents at least one element selected from the group consisting of B, P, K, Zn and Te; and the indexes a, b, c, d and e represent an atomic composition, where when a is 1, b, c and d are $0.05 \leq b \leq 10$, $0.001 \leq c \leq 10$, and $0 \leq d \leq 5$, and e represents the number of oxygen atoms corresponding to the oxide produced when the above components are combined.

As the ammoxidation catalyst of this type, many catalysts have conventionally been proposed. For instance, a metallic oxide comprising molybdenum and bismuth, and a metallic oxide comprising antimony and tin or iron or uranium, such as those described in Japanese Patent Publications No. 5870/1961, No. 13460/1962 and No. 14075/1962, Japanese Patent Laid-Open Publications No. 58100/1974 (the specification of U.S. Pat. No. 3,911,089) and No. 10200/1976, Japanese Patent Publications No. 33888/1976 (the specification of British Patent No. 1,319,190) and No. 18014/1978 (the specifications of U.S. Pat. Nos. 3,988,359 and 4,083,804), and Japanese Patent Laid-Open Publication No. 257125/1989 (the specification of U.S. Pat. No. 5,158,787) have been known to be effective for the ammoxidation of methanol, propylene or isobutylene.

These catalysts can be readily obtained according to the details which will be described in the following with respect to <Ammoxidation of Methanol>.

The fluidized solid matter contained in the fluidized bed in the present invention is composed of the particles of such an ammoxidation catalyst, and, when necessary, other solid particles such as silica or alumina particles having small surface areas, or catalyst particles deactivated by high-temperature calcination.

In the present invention, the term "the density of the fluidized solid matter" means the density of the solid matter including the above-described particles having extremely low chemical and catalytic actions on reaction as compared with those of the catalyst, or having no such actions.

Upon practicing the present invention, the particle diameters of the catalyst particles are in the range of approximately 10 to 500 micrometers, and the mean particle diameter is from 30 to 200 micrometers, preferably from 40 to 100 micrometers. The bulk density of the catalyst is in the range of 0.5 to 2 $g/cm^3$, preferably 0.7 to 1.5 $g/cm^3$. The height of the stationary catalyst bed is in the range of 0.1 to 10 m, preferably 1 to 5 m. The starting gas to be fed to the reaction column is such that the molar ratio of oxygen/hydrocarbon or the like is in the range of 0.5 to 5, preferably 1 to 3 and that the molar ratio of ammonia/hydrocarbon or the like is in the range of 0.5 to 3, preferably 0.7 to 1.5. The gas velocity is in the range of 0.1 to 1 m/s, preferably 0.3 to 1 m/s; the reaction temperature is in the range of 350 to 500° C.; the contact time is in the range of 0.1 to 30 seconds, preferably 0.5 to 20 seconds; and the reaction pressure is from atmospheric pressure to 2 $kg/cm^2G$.

<Ammoxidation of Methanol>

Objective compounds of ammoxidation which is carried out by the method of the present invention are a wide variety of compounds including methanol. These objective compounds are all industrially useful when the utility of their ammoxidized products, that is, nitriles, is taken into consideration. However, the production of hydrocyanic acid by means of the ammoxidation of methanol is particularly significant because the resulting nitrile has a relatively simple structure, and can further be subjected to various reactions.

The conditions of this specific ammoxidation are the same as those of the above-described ammoxidation. However, an explanation which is directed only to this specific ammoxidation is as follows.

The present invention also relates in particular to a method for carrying out the vapor-phase catalytic ammoxidation of methanol in a fluidized-bed reactor. More particularly, the present invention is to provide an industrially advantageous method for ammoxidizing methanol, in which the catalytic activity is maintained high to attain high yield of hydrocyanic acid.

Hydrocyanic acid is produced by the decomposition of formamide, by the reaction between methane and ammonia, by the ammoxidation reaction of methane, or the like. Further, hydrocyanic acid is, in most cases, obtained as a by-product when acrylonitrile is produced by means of the ammoxidation of propylene. However, in recent years, the use of hydrocyanic acid derivatives such as acetone cyanohydrin and adiponitrile has been extended, and the demand for sodium cyanide which is used for the recovery of gold has been increased. Hydrocyanic acid may therefore be in short supply.

In view of such circumstances, the present invention was accomplished in order to newly develop an industrially advantageous method for producing hydrocyanic acid by means of the ammoxidation of methanol.

As a method for producing hydrocyanic acid by means of the ammoxidation of methanol, there have been known a method using a molybdenum oxide catalyst as described in Russian Patent No. 106,226, a method using an oxide catalyst containing molybdenum, bismuth and other various elements as described in Japanese Patent Publication No. 35400/1976, a method using an oxide catalyst containing antimony and at least one element selected from the group consisting of iron, cobalt, nickel, manganese, zinc and uranium as described in Japanese Patent Publication No. 39839/1979, a method using an oxide catalyst containing manganese and phosphorus as described in the specification of U.S. Pat. No. 4,457,905, a method using an antimony phosphate catalyst as described in the specification of U.S. Pat. No. 4,511,548, and the like.

Further, in order to improve the iron-antimony oxide catalyst described in Japanese Patent Publication No. 39839/1979, we proposed an oxide catalyst containing iron, copper and antimony as described in Japanese Patent Laid-Open Publication No. 145617/1983, an oxide catalyst containing iron, copper, antimony and phosphorus as described in Japanese Patent Publication No. 64555/1995, and a catalyst containing iron, antimony and phosphorus as essential components, and iron antimonate as a crystalline phase, as described in Japanese Patent Laid-Open Publication No. 26342/1991. In addition, we also proposed, as methods for preparing the catalysts, those methods which are described in Japanese Patent Publications No. 12434/1995 and No. 63629/1995, and the like. By these methods, improvements have been made on many points. However, in order to industrially practice these methods, it would be preferable to further improve some points.

When hydrocyanic acid is produced by means of the ammoxidation of methanol, it may be necessary in a conventional method that the ratio of ammonia or oxygen to methanol contained in a feed gas be made high in order to retain the catalytic activity. However, even when such a reaction condition is employed, the problems of economical efficiency and of safety still remain unsolved. In general, the following method is employed to recover hydrocyanic acid from a reaction product: a reaction product at a high temperature is cooled, and then allowed to be absorbed in a solvent such as water, and the absorbed liquid is subjected to distillation to separate hydrocyanic acid therefrom. During this operation, hydrocyanic acid can be polymerized when ammonia is present in the system. This is not only a loss of hydrocyanic acid, but also the cause of the clogging of the apparatus used. It is therefore necessary to separate and remove ammonia at the stage of cooling, for example, by treating the reaction product with an acid for neutralization. However, when ammonia is fed excessively to methanol, the amount of ammonia used per amount of HCN produced is increased, the amount of the acid required for neutralizing unreacted ammonia is increased, and the cost for constructing a plant which is used for removing salts produced by the neutralization treatment is required. This conventional method is thus disadvantageous from the economical point of view.

Further, when the ratio of oxygen to methanol is high, a large quantity of nitrogen which is not needed for the reaction is to be fed to the reaction system because air is generally used as the source of oxygen. As a result, the volumetric efficiency of the reactor is lowered. Moreover, when the concentration of oxygen contained in the reaction product is increased, the reaction product can get into the explosion range so that it has a danger of explosion.

For the above-described reasons, it is desirable that the ratio of ammonia or oxygen to methanol contained in a feed gas be low. However, when this ratio is low, hydrocyanic acid is produced in a decreased yield, and the catalyst can undergo deterioration in catalytic activity with time.

The present invention was accomplished in order to overcome the aforementioned shortcomings in the prior art.

An object of the present invention is therefore to provide an economically advantageous method in which reaction can be effectively carried out even under such a reaction condition that the ratio of ammonia or oxygen to methanol contained in a feed gas is low, and the desired product, that is, hydrocyanic acid, can be obtained at high yield with high selectivity and stably with time.

We studied industrial methods for producing hydrocyanic acid by carrying out the vapor-phase catalytic ammoxidation of methanol in a fluidized-bed reactor, and, as a result, found the following: when methanol, ammonia and steam are respectively fed to the reaction system from specific positions, an oxide catalyst containing specific elements such as iron, antimony, phosphorus and copper can improve the efficiency of the utilization of ammonia and oxygen; the oxidation-reduction stability of the catalyst is remarkably increased, so that the catalyst hardly undergoes deterioration; and hydrocyanic acid can be obtained in high yield even if the reaction is carried out under such a condition that the ratio of ammonia or oxygen to methanol is low. The present invention has been accomplished on the basis of these findings.

Accordingly, the present invention relates to a method for ammoxidizing methanol, in which, when the vapor-phase catalytic ammoxidation of methanol is carried out in a fluidized-bed reactor under the previously-mentioned general conditions for ammoxidation to obtain hydrocyanic acid, the reaction is carried out by using, as a catalyst, a metallic oxide containing [I] at least one element selected from the group consisting of iron, antimony, phosphorus and copper, and [II] at least one element selected from the group consisting of vanadium, manganese, molybdenum, tungsten and bismuth, by feeding, to the catalyst bed, an oxygen-containing gas through feed openings provided at the lower part of the reactor, and methanol and ammonia as a steam-containing gas through feed openings provided above the feed openings for the oxygen-containing gas, or by feeding all of or a part of the steam to the catalyst bed through feed openings provided below the feed openings for methanol and ammonia, with the molar ratio of steam to methanol adjusted to 0.1 to 3.

An example of the present invention specific to the ammoxidation of methanol will now be explained. The disclosure which will be given below on this particular ammoxidation applies, whenever applicable, to the ammoxidation given hereinabove in general terms.

In the method of the present invention, it is important to carry out the ammoxidation reaction of methanol by using a metallic oxide catalyst containing specific elements such as iron, antimony, phosphorus and copper, and by feeding methanol, ammonia and steam to a specific reaction zone.

<Catalyst(bis)>

The catalyst for use in the method of the present invention is a metallic oxide composition containing [I] at least one element selected from the group consisting of iron, antimony, phosphorus and copper, and [II] at least one element selected from the group consisting of vanadium, manganese, molybdenum, tungsten and bismuth. The atomic ratio of the element [I]: the element [II] is preferably in the range of (20 to 100):(0.5 to 5). This catalyst shows excellent performance when steam is present in the reaction system, and when the catalyst bed density is low, so that hydrocyanic acid can be produced with high production efficiency. A preferable catalyst is an oxide composition comprising iron, antimony, phosphorus and vanadium. The vanadium content of this oxide composition is at least 0.6, preferably from 0.6 to 3, for 10 of iron when expressed in atomic ratio.

More specifically, preferable catalysts are oxide compositions represented by the following empirical formula (B):

$$Fe_{a'}Sb_{b'}P_{c'}V_{d'}Mo_{e'}Cu_{f'}W_{g'}X_{h'}Y_{i'}Z_{j'}O_{k'}(SiO_2)_{l'}$$ (B)

wherein Fe, Sb, P, V, Mo, Cu and W represent iron, antimony, phosphorus, vanadium, molybdenum, copper and tungsten, respectively; X represents at least one element selected from the group consisting of Mg, Zn, La, Ce, Al, Cr, Mn, Co, Ni, Bi, U and Sn, preferably at least one element selected from the group consisting of Mg, Zn, Al, Mn, Co and Ni; Y represents at least one element selected from the group consisting of B and Te; Z represents at least one element selected from the group consisting of Li, Na, K, Rb, Cs, Ca and Ba; the indexes a', b', c', d', e', f', g', h', i', j', k' and l' represent an atomic ratio, where, when a' is 10, b' is from 12 to 30, preferably from 15 to 27, c' is from 1 to 30, preferably from 3 to 20, more preferably from 5 to 15, provided that b'/c' is larger than 1.5, d' is from 0.6 to 3, preferably from 0.8 to 2.8, more preferably from 1 to 2.5, e' is from 0 to 0.3, f' is from 0 to 5, g' is from 0 to 3, h' is from 0 to 6, i' is from 0 to 5, j' is from 0 to 3, k' is a number corresponding to the oxide produced when the above components are combined, and l' is from 0 to 200.

The catalyst represented by the above empirical formula (B) contains as its main components iron, antimony, phosphorus and vanadium. It is not clear how these components form compounds in the catalyst to give effects on activity and physical properties. However, when the composition of the above catalyst exceeds the range defined by the above empirical formula, the selectivity to hydrocyanic acid is lowered, or the properties of the catalyst are impaired, and, as a result, it sometimes becomes difficult to attain the object. It is therefore considered that the elements constituting the catalyst are closely related to one another to reveal the effects. In particular, it is preferable that iron antimonate be present in the catalyst to form a crystalline phase. The vanadium component is considered to be dissolved in this crystalline phase in a solid state. The presence of iron antimonate is effective for increasing the yield of hydrocyanic acid, for preventing the lowering of the yield in the course of long-time operation, and for imparting suitable properties to the catalyst.

In the ammoxidation reaction of propylene, it has been known that the addition of the vanadium, molybdenum or tungsten component to a catalyst containing iron and antimony is effective for increasing the reaction rate, and for improving the resistance to deterioration by reduction. In particular, the vanadium component has an excellent action on a catalyst containing iron, antimony and phosphorus. Actually, when a specific amount of the vanadium component was added to the catalyst, the resulting catalyst revealed such a notable effect that hydrocyanic acid was obtained in high yield with high selectivity, and also stably with time even when the ratio of oxygen to methanol contained in a starting gas to be fed to the reaction system was made low, that is, the concentration of the starting methanol was made high. The molybdenum and tungsten components have no such a notable effect. This is a fact which would not be expected by the conventional knowledge.

The addition of the copper component and the X component is effective for preventing the formation of protrusion on the surface of the catalyst, which tends to be particularly caused when the antimony content is high, for improving the strength of the catalyst, and for regulating the reaction rate and catalytic properties. The addition of the Y component contributes to the improvement on selectivity; and the addition of the Z component contributes to the control of reaction rate and by-product.

The catalyst for use in the present invention can be used as it is without using a carrier. It is, however, preferable to use the catalyst having a silica carrier to support it. The amount of the carrier can be freely changed within a range of 10 to 90% by weight of the total weight of the catalyst.

The above-described catalyst of a formula (B) can be prepared by any known method. For example, a method described in Japanese Patent Publication No. 12434/1995 or No. 63629/1995, Japanese Patent Laid-Open Publication No. 26342/1991, or the like can be used.

As described hereinabove with respect to the catalysts of a formula (A), the following will apply also to the production of the catalysts of a formula (A) where applicable.

A starting material for each component of the catalyst can be selected from various types of compounds such as metallic oxides, oxides, hydroxides, chlorides and nitrates of the component. Further, those compounds which can be transformed into oxides by a chemical treatment or calcination treatment can also be used.

As a starting material for the iron component, an iron oxide such as ferrous oxide, ferric oxide or triiron tetraoxide, a mineral acid salt of iron such as ferrous chloride, ferric chloride, ferric nitrate, iron carbonate, or a product obtained by oxidizing metallic iron with nitric acid, or an organic acid salt of iron such as iron oxalate or iron citrate can be used.

As a starting material for the antimony component, antimony trioxide, antimony tetroxide, antimony pentoxide, antimonic acid, polyantimonic acid, sodium antimonate, potassium antimonate, antimony trichloride, antimony pentachloride or the like can be used. Further, a product obtainable by oxidizing metallic antimony with nitric acid can also be used.

As a starting material for the phosphorus component, it is preferable to use phosphorus pentoxide, orthophosphoric acid, ammonium dihydrogenphosphate, diammonium hydrogenphosphate, triammonium phosphate, or the like.

As a starting material for the vanadium component, vanadium pentoxide, ammonium metavanadate, vanadyl oxalate, vanadyl sulfate or the like can be used.

As a starting material for the copper component, cuprous oxide, cupric oxide, copper nitrate, or the like is used.

As a starting material for the molybdenum component, molybdenum trioxide, molybdic acid, ammonium paramolybdate, ammonium metamolybdate, a molybdenum halide, or the like is used. As a starting material for the tungsten component, tungsten trioxide, ammonium paratungstate, ammonium metatungstate, tungstic acid, or the like is used.

As a starting material for the tin component, stannous oxide, stannic oxide, or the like is used.

As starting materials for the X, Y and Z components, oxides, hydroxides, sulfates, carbonates, organic acid salts, and the like of these elements can be respectively used.

It is preferable to use silica sol as a material for the silica carrier. However, silica hydrogel, fumed silica or the like can also be used as a part of or all of the silica sol.

The fluidized-bed catalyst may be prepared in the following manner: a mixed slurry of materials containing the components of the catalyst is prepared; the slurry prepared is subjected to pH adjustment (the pH being adjusted to approximately 7 or lower, preferably about 1 to about 4), a heat treatment (heating to approximately 40 to 150° C.), or the like, as needed; thereafter, the slurry is spray-dried, and the resulting fine particles are subjected to calcination.

Calcination is important for imparting predetermined activity to the catalyst. It is preferable to conduct the calcination at a temperature ranging from 200 to 900° C., preferably from 400 to 850° C., for 0.5 to 10 hours. There is no particular limitation on the atmosphere in which the calcination is conducted although a reducing atmosphere would not be recommended, and the calcination can be conducted either in an atmosphere of an oxidizing gas containing oxygen, or in an atmosphere of an inert gas containing nitrogen only. In general, it is preferable to conduct the calcination in an atmosphere of air for reasons of economy. A tunnel kiln, rotary kiln or fluidized kiln can be used for the calcination.

The size of the catalyst can be selected depending upon the purpose. The fluidized-bed catalyst is generally used as particles having particle diameters ranging from 10 to 200 microns.

<Reaction in Fluidized Bed(bis)>

Figure 2:
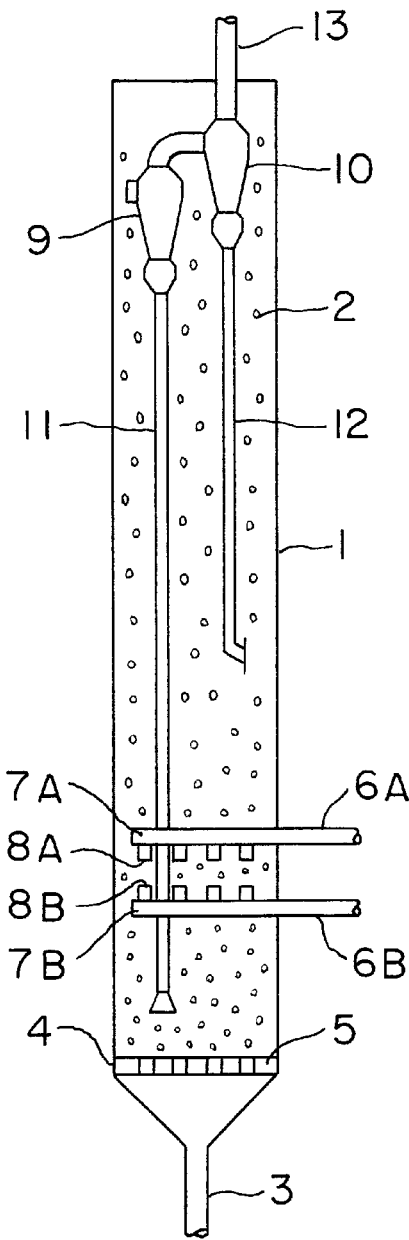
FIG. 2 is a sectional view of a reactor which is used for carrying out the ammoxidation of methanol in accordance with the method of the present invention, where 6A: (methanol+ammonia) mixed gas feed pipe, 7A: a gas dispersing means, 8A: openings for the gas dispersing means, 6B: a steam feed pipe, 7B: a gas dispersing means, and 8B: openings for the gas dispersing means; the remaining parts being indicated by the same symbols as those used in FIG. 1.

A preferable embodiment of this specific method of the present invention is, for example, one which is shown in FIG. 2. The apparatus shown in FIG. 2 is the same as that shown in FIG. 1 except the means for introducing methanol and ammonia (6A, 7A and 8A), and the means for introducing steam (6B, 7B and 8B); and like numerals in these two figures designate corresponding parts. The numeral 1 indicates a reactor, the numeral 8A indicates feed openings for a mixed gas of methanol+ammonia, or the like, the numeral 8B indicates feed openings for steam, the numeral 4 indicates feed openings for an oxygen-containing gas, and the numeral 2 indicates a catalyst. This specific example of the present invention in respect of the ammoxidation of methanol is not limited only to the extent specifically shown in FIG. 2.

A catalyst 2 is housed in a reactor 1. An oxygen-containing gas is introduced into the reactor 1 through a pipe 3, and fed to the lower part of the catalyst bed through openings, viz. feed openings 4 for an oxygen-containing gas, formed in a gas-dispersing apparatus 5. Methanol and ammonia are mixed with steam, and the resulting mixture is introduced into the reactor 1 through a pipe 6A which is provided above the feed openings 4 for the oxygen-containing gas, and fed into the catalyst bed through openings, viz. feed openings 8A for a mixed gas of methanol+ammonia, etc. formed in a gas-dispersing apparatus 7A. It is possible, when necessary, to introduce at least a part of the steam into the reactor 1 through a pipe 6B which is provided below the feed openings BA for methanol and ammonia so as to divisionally feed the steam into the catalyst bed through feed openings, viz. feed openings 8B for water vapor, formed in a gas-dispersing apparatus 7B. Alternatively, at least a part of the steam is mixed with the oxygen-containing gas, and the mixture is fed into the catalyst bed through the gas-dispersing means 5. At the upper part of the reactor 1 is provided a multicyclone composed of cyclones 9 and 10 arranged in series. The catalyst particles accompanied by the gas stream are separated therefrom by this multicyclone, and returned to the lower or middle part of the catalyst bed through a pipe 12 or 11. The oxygen-containing gas which is fed to the lower part of the reactor 1 is, in general, air. However, oxygen-enriched air, or oxygen diluted with an inert gas can also be used instead of air.

Here again, the feed openings for the oxygen-containing gas are means for feeding the oxygen-containing gas to the catalyst bed which is fluidized, and the site of or, when the reactor is vertical, the level or height of the feed openings for the oxygen-containing gas may typically define the bottom of the catalyst fluidized bed.

In the method of the present invention of ammoxidation of methanol, it is preferable to control the amount of the steam to be fed to the reactor so that the molar ratio of steam to methanol will be from 0.1 to 3. Further, it is preferable to practice the method of the present invention of this specific embodiment by adjusting the molar ratio of oxygen to methanol contained in the feed gas to less than 1.6, preferably from 0.8 to 1.5, and the molar ratio of ammonia to methanol in the feed gas to less than 1.2, preferably 0.7 to 1.1. The concentration of methanol in the feed gas can be changed within a range of 3 to 20%.

In this specific embodiment of the present invention, too, the position of the feed openings for a mixed gas such as a mixture of methanol and ammonia cannot be determined only by the shape, the size and the like of the reactor. However, when the reactor is cylindrical, they may be provided above the feed openings for an oxygen-containing gas, provided that the distance between the feed openings for an oxygen-containing gas and those for a mixed gas is from 30 to 250% of the height of the fluidized catalyst bed in a static state, viz. the height of the stationary catalyst bed. Steam can be fed after mixed with methanol and ammonia. Alternatively, all of or a part of the steam can be fed to the catalyst bed from a position below the feed openings for a mixed gas such as a mixture of methanol and ammonia. The divisional feeding of steam can be attained either by allowing steam to exist in an oxygen-containing gas, or by feeding steam to the catalyst bed through feed openings which are separately provided for the feeding of steam. The quantity of steam which can be divisionally fed is from 5 to 95%, preferably from 20 to 90%, of the whole quantity of steam to be fed to the reactor. Methanol and ammonia can be fed either by mixing the whole quantity of methanol with that of ammonia. Alternatively, they can be fed in divided quantities.

In this specific example of the present invention, when the reaction is carried out by using the catalyst under such a condition that the catalyst bed density is low, the state of contact between the gas and the catalyst can be made good, so that hydrocyanic acid can be obtained in high yield. The catalyst bed density at the position of the feed openings for methanol and ammonia is from 50 to 300 kg/m$^3$, preferably from 100 to 250 kg/m$^3$. In general, a high gas velocity is employed in order to obtain a catalyst density in the above-described range. However, in the method of the present invention, the state of contact between the gas and the catalyst can be maintained excellent even when the gas velocity is made as low as 1 m/sec or lower. Namely, it is important to decide the position of the feed openings for methanol and ammonia, and to select the dividing ratio of steam so that the above-described catalyst bed density can be obtained under given reaction conditions. The catalyst bed density can be determined by obtaining the difference between static pressures measured at two different points on the fluidized bed in the direction of the height thereof, and dividing the difference by the distance between the two points. Therefore, the catalyst bed density at the feed openings for methanol and ammonia can be estimated from the distribution of the density in the direction of the height of the fluidized bed.

By feeding steam to the catalyst bed, the efficiency of the utilization of ammonia and oxygen is improved. In particular, the oxidation-reduction stability of the catalyst is remarkably improved, so that the catalyst hardly undergoes deterioration. Moreover, the yield of hydrocyanic acid is not decreased even when the ratio of ammonia or oxygen to methanol is made low. This specific method of the present invention is thus advantageous from the industrial point of view.

The reaction temperature for the particular ammoxidation is in the range of 350 to 500° C., preferably 380 to 470° C. The reaction can be carried out under atmospheric, superatmospheric, or subatmospheric pressure conditions. It is however suitable that the reaction pressure be from a pressure near atmospheric pressure to a pressure of 2 kg/cm$^2$, Gauge.

The contact time is in the range of 0.01 to 20 seconds, preferably 0.05 to 10 seconds, particularly 0.1 to 6 seconds, on the basis of the volume of the gas at the reaction temperature under the reaction pressure.

EXAMPLES

The following Examples are to illustrate the constitution and effects of the present invention more specifically.

The height of a stationary catalyst bed, the relative height "H" of the feed openings for a starting hydrocarbon or the like, the gas velocity, the yield of a nitrite, and the conversion of a starting hydrocarbon or the like, used in this Specification are defined as follows.

Height of stationary catalyst bed [m]=(amount of catalyst packed [kg])/{(bulk density of catalyst [kg/m$^3$])× (effective sectional area of reactor [m$^2$])}

H [%]={(distance between feed openings for oxygen-containing gas and those for starting hydrocarbon or the like [m])/(height of stationary catalyst bed [m])}×100

Gas velocity [m/s]=(volume velocity of whole feed gas under reaction conditions [m$^3$/s])/(effective sectional area of reactor [m$^2$])

Yield of nitrile [%]={(weight of carbon contained in nitrile produced [kg]/(weight of carbon contained in starting hydrocarbon or the like fed [kg])}×100

Conversion of starting hydrocarbon or the like [%]={ (weight of carbon contained in starting hydrocarbon or the like reacted [kg])/(weight of carbon contained in starting hydrocarbon or the like fed [kg])}×100

Comparative Example A1

Hydrocyanic acid was synthesized by carrying out the ammoxidation reaction of methanol in a fluidized-bed reactor by the use of an iron-antimony-phosphorus-copper-vanadium-molybdenum fluidized bed catalyst supported on a silica carrier. A reactor having an inner diameter of approximately 0.2 m and a height of 5 m was used for this reaction. Air was fed from the bottom of this reactor, and a mixed gas of methanol and ammonia was fed from the position 0.2 m above the feed openings for air. A cyclone is provided at the upper part of the reactor, and those catalyst particles which come out of the catalyst bed and are transported or accompanied by the gas are collected by this cyclone. These catalyst particles are then returned to the position 0.15 m above the feed openings for air, through a vertical pipe having an inner diameter of 0.037 m, attached to the lower part of the cyclone, so as to feed them back to the catalyst bed.

40 kg of the catalyst was packed in this reactor. At this time, the height of the stationary catalyst bed was 1.04 m, the relative height "H" of the feed openings for methanol was 19%, and the catalyst bed density at the height "H" was 510 kg/m$^3$.

By controlling the composition of the gases to be fed to the reactor so that the molar ratio of oxygen/methanol would be 1.36 and that the molar ratio of ammonia/methanol would be 1.0, and by regulating the gas velocity to 0.5 m/s, the reaction was carried out at a temperature of 430° C. under a pressure of 0.5 kg/cm$^2$G. The results of the reaction were such that the yield of hydrocyanic acid was 82.0% and that the conversion of methanol was 99.9%.

Example A1

Hydrocyanic acid was synthesized by carrying out the ammoxidation reaction of methanol by the use of the same reactor and catalyst as those used in Comparative Example A1. The reaction was carried out in the same manner as in Comparative Example A1 except that the relative height "H" of the feed openings for methanol was changed to 108% and that the reaction temperature was changed to 440° C. In order to make the height "H" to 108%, the feed openings for methanol were provided at the position 0.7 m above the feed openings for air which were positioned at the bottom of the reactor. Further, the catalyst was packed in the reactor in an amount of 25 kg to make the height of the stationary catalyst bed to 0.65 m. At this time, the catalyst bed density at the height "H" was 200 kg/m$^3$.

The results of the reaction were such that the yield of hydrocyanic acid was 92.0% and that the conversion of methanol was 98.5%. It was thus found that the yield of hydrocyanic acid obtained in this example was considerably higher than that of hydrocyanic acid obtained in Comparative Example A1. It is noted that the reason why the reaction temperature was raised to a temperature 10° C. higher than that in Comparative Example A1 is to ensure the sufficient conversion of methanol. However, a difference of 10° C. in reaction temperature has only a slight influence on the yield of hydrocyanic acid as long as the conversion of methanol is in a specific range. It is therefore reasonable to compare Example A1 with Comparative Example Al to show the critical significance of the difference in the position of the feed openings for the starting material and in the density of the catalyst.

Example A2

Hydrocyanic acid was synthesized by carrying out the ammoxidation reaction of methanol by the use of the same reactor and catalyst as those used in Comparative Example A1. The reaction was carried out in the same manner as in Comparative Example A1 except that the relative height "H" of the feed openings for methanol was changed to 144% and that the reaction temperature was changed to 445° C. In order to make the height "H" to 144%, the feed openings for methanol were provided at the position 1.5 m above the feed openings for air which were positioned at the bottom of the reactor. Further, the catalyst was packed in the reactor in an amount of 40 kg to make the height of the stationary catalyst bed to 1.04 m. At this time, the catalyst bed density at the height "H" was 180 kg/m$^3$.

The results of the reaction were such that the yield of hydrocyanic acid was 91.5% and that the conversion of methanol was 97.6%. It was thus found that the yield of hydrocyanic acid obtained in this Example A2 was considerably higher than that of hydrocyanic acid obtained in Comparative Example A1.

Comparative Example A2

Acrylonitrile was synthesized by carrying out the ammoxidation reaction of propylene by the use of the same reactor as that used in Comparative Example A1, and a molybdenum-bismuth-nickel-iron-antimony-potassium catalyst supported on silica. The relative height "H" of the feed openings for a mixed gas of propylene and ammonia was made to 15%. In order to make the height "H" to 15%, the feed openings for propylene were provided at the position 0.2 m above the feed openings for air which were positioned at the bottom of the reactor. Further, the catalyst was packed in the reactor in an amount of 40 kg to make the height of the stationary catalyst bed to 1.35 m. At this time, the catalyst bed density at the height "H" was 460 kg/m$^3$.

By controlling the composition of the gases to be fed to the reactor so that the molar ratio of oxygen/propylene would be 2.1 and that the molar ratio of ammonia/propylene would be 1.2, and by regulating the gas velocity to 0.5 m/s, the reaction was carried out at a temperature of 430° C. under a pressure of 0.5 kg/cm$^2$G.

The results of the reaction were such that the yield of acrylonitrile was 78.0% and that the conversion of propylene was 99.3%.

Example A3

Acrylonitrile was synthesized by carrying out the ammoxidation reaction of propylene by the use of the same reactor and catalyst as those used in Comparative Example A2. The reaction was carried out in the same manner as in Comparative Example A2 except that the relative height "H" of the feed openings for propylene was changed to 65%. In order to make the height "H" to 65%, the feed openings for propylene were provided at the position 1.1 m above the feed openings for air which were positioned at the bottom of the reactor. Further, the catalyst was packed in the reactor in an amount of 50 kg to make the height of the stationary catalyst bed to 1.69 m. At this time, the catalyst bed density at the height "H" was 230 kg/m$^3$.

The results of the reaction were such that the yield of acrylonitrile was 81.2% and that the conversion of propylene was 98.5%. The yield of acrylonitrile obtained in this example was thus higher than that of acrylonitrile obtained in Comparative Example A2.

In examples of the present invention, specified to the ammoxidation of methanol, the height of a stationary catalyst bed, the contact time (sec), the yield of hydrocyanic acid, the conversion of methanol, and the height of the feed openings for methanol are defined as follows.

Height of stationary catalyst bed [m]=(amount of catalyst packed [kg])/{(bulk density of catalyst [kg/m$^3$])×(effective sectional area of reactor [m$^2$])}

Contact time (sec)=(volume of catalyst in static state, existing above feed openings for methanol gas [m$^3$])/(volume flow rate of whole feed gas under reaction conditions [m$^3$/sec])

Yield of hydrocyanic acid [%]={(weight of carbon contained in hydrocyanic acid produced [kg])/(weight of carbon contained in methanol fed [kg])}×100

Conversion of methanol (%)={(weight of carbon contained in methanol reacted [kg]/(weight of carbon contained in methanol fed [kg])}×100

Height "H" of feed openings for methanol (%)={(distance between feed openings for oxygen-containing gas and those for methanol [m])=/(height of stationary catalyst bed [m])}×100

Catalysts used for the following reactions, and methods for preparing the same are as follows.

[Catalyst 1]

A catalyst having the empirical formula:

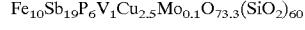

was prepared in the following manner.

(I) 247.3 g of antimony trioxide powder was taken.

(II) 385 ml of nitric acid (specific gravity: 1.38) and 480 ml of water were mixed, and the mixture was heated. 49.9 g of electrolytic iron powder was gradually added to, and dissolved in the mixture. Subsequently, 54.0 g of copper nitrate was added to, and dissolved in this solution.

(III) 10.5 g of ammonium metavanadate and 1.6 g of ammonium paramolybdate were dissolved in 300 ml of water.

(IV) 1,612 g of silica sol (SiO$_2$: 20 wt. %) was taken.

(IV), (I) and (III) were successively added to (II) in the mentioned order with stirring. The pH of this mixture was adjusted to 2 by the addition of 15% aqueous ammonia. The resulting slurry was heat-treated at 98° C. for 3 hours with stirring, and 61.8 g of phosphoric acid (content 85%) was then added to the slurry. The mixture was thoroughly stirred. Subsequently, the slurry was spray-dried by a rotary-disc-type spray drier. The fine spherical particles thus obtained were calcinated at 200° C. for 2 hours, at 500° C. for 3 hours, and at 800° C. for 3 hours.

[Catalyst 2]

A catalyst having the empirical formula:

$$Fe_{10}Sb_{19}P_8V_1Cu_2O_{77.5}(SiO_2)_{60}$$

was prepared in the same manner as in the case of Catalyst 1.

[Catalyst 3]

A catalyst having the empirical formula:

$$Fe_{10}Sb_{20}P_{10}V_{1.2}B_{0.2}O_{83.3}(SiO_2)_{80}$$

was prepared in the same manner as in the case of Catalyst 1, except that boric anhydride was used as a starting material for the component B and that a solution of this boric anhydride in water was added after the addition of antimony trioxide power.

<Catalyst 4>

A catalyst having the empirical formula:

$$Fe_{10}Sb_{25}P_{14}V_{2.5}Mn_{2.5}O_{111.25}(SiO_2)_{80}$$

was prepared in the same manner as in the case of Catalyst 1, except that manganese nitrate was used as a starting material for the Mn component and that a solution of this manganese nitrate in water was added after the addition of antimony trioxide power.

Comparative Example B1

43.3 kg of Catalyst 1 was packed in a fluidized-bed reactor having an inner diameter of 20 cm and a height of 5 m (the height of the stationary catalyst bed: 120 cm). Air was fed from the bottom of this reactor, and a mixed gas of methanol and ammonia was fed from the position 30 cm above the feed openings for air. By controlling the composition of the gases to be fed to the reactor so that the molar ratio of oxygen/methanol would be 1.15 and that the molar ratio of ammonia/methanol would be 1.0, and by regulating the gas velocity to 50 cm/s, the reaction was carried out at a temperature of 430° C. under a pressure of 0.5 kg/cm$^2$G. At this time, the contact time was 2.0 seconds, the height "H" of the feed openings for methanol was 25%, and the catalyst bed density at the height "H" was 460 kg/m$^3$. The results of the reaction were as follows: at one hour after the initiation of the reaction, the yield of hydrocyanic acid was 82.1% and the conversion of methanol was 99.2%; and at 20 hours after the initiation of the reaction, the yield of hydrocyanic acid was 80.1% and the conversion of methanol was 99.0%. It was thus found that the yield of hydrocyanic acid was lowered with time.

Example B1

The ammoxidation reaction of methanol was carried out in the same manner as in Comparative Example B1, except that a mixed gas of methanol and ammonia, to which steam had been added was fed to the reactor from the position 70 cm above the feed openings for air which were positioned at the lower part of the reactor. The molar ratio of the water vapor to methanol was adjusted to 1.0. At this time, the contact time was 1.4 seconds, the height "H" of the feed openings for methanol was 58%, and the catalyst bed density at the height "H" was 220 kg/m$^3$. The results of the reaction were as follows: at one hour after the initiation of the reaction, the yield of hydrocyanic acid was 84.5% and the conversion of methanol was 98.6%; and at 20 hours after the initiation of the reaction, the yield of hydrocyanic acid was 84.0% and the conversion of methanol was 98.3%. It was thus found the following: the yield of hydrocyanic acid obtained in Example B1 was higher than that of hydrocyanic acid obtained in Comparative Example B1; the yield of hydrocyanic acid was not lowered with time; and improvement in the results of the reaction and the stabilization of the catalytic activity can be attained at the same time.

Comparative Example B2

In a fluidized-bed reactor having an inner diameter of 4 cm and a height of 1.5 m, 20 pieces of 2 mm thick perforated plates, each having perforations having a diameter of 2 mm with an opening rate of approximately 40%, were placed with an interval of 5 cm, the lowermost plate being placed at the position 7 cm above the feed openings for air provided at the lower part of the reactor. 538 g of Catalyst 2 was packed in this reactor (the height of the stationary catalyst bed: 40 cm). The ammoxidation reaction of methanol was carried out by feeding air from the lower part of the reactor, and a mixed gas of methanol and ammonia from the position 10 cm above the feed openings for air, with the composition of the gases changed by three steps in the following manner: the molar ratio of oxygen/methanol was controlled to 1.36 and that of ammonia/methanol was controlled to 1.0 for the first 3 hours; the molar ratio of oxygen/methanol was controlled to 0.91 and that of ammonia/methanol was controlled to 0.67 for the next 2 hours; and the molar ratio of oxygen/methanol was controlled to 1.36 and that of ammonia/methanol was controlled to 1.0 for the last 3 hours. Thus, the reaction was carried out for 8 hours in total. During this reaction, the reaction temperature was adjusted to 430° C., the reaction pressure was adjusted to 0.5 kg/cm$^2$G, and the gas velocity was adjusted to 15 cm/s. At this time, the contact time was 1.7 seconds, the height "H" of the feed openings for methanol was 25%, and the catalyst bed density at the height "H" was 730 kg/m$^3$. The results of the reaction were as follows: at one hour after the initiation of the reaction, the yield of hydrocyanic acid was 82.4% and the conversion of methanol was 99.6%; and at 8 hours after the initiation of the reaction, the yield of hydrocyanic acid was 77.5% and the conversion of methanol was 95.5%. The yield of hydrocyanic acid was thus found to be lowered with time.

Example B2

The ammoxidation reaction of methanol was carried out in the same manner as in Comparative Example B2, except that a mixed gas of methanol and ammonia was fed from the position 30 cm above the feed openings for air which were positioned at the lower part of the reactor and that air mixed with steam was fed to the reactor for 2 hours at the middle stage of the reaction. The molar ratio of the steam to methanol was adjusted to 0.67. At this time, the height "H" of the feed openings for methanol was 75%, and the catalyst bed density at the height "H" was 250 kg/m$^3$. The results of the reaction were as follows: at one hour after the initiation of the reaction, the yield of hydrocyanic acid was 85.9% and the conversion of methanol was 98.1%; and at 8 hours after the initiation of the reaction, the yield of hydrocyanic acid was 86.1% and the conversion of methanol was 98.3%. The yield of hydrocyanic acid in Example B2 was not so lowered with time as compared with that in Comparative Example B2. It is thus found that the catalyst hardly undergoes deterioration in catalytic activity because it is stabilized even under such a reaction condition that the ratio of oxygen to methanol is low.

Comparative Example B3

44.5 kg of Catalyst 2 was packed in the same reactor as that used in Comparative Example B1 (the height of the stationary catalyst bed: 120 cm). Air was fed from the lower part of this reactor, and a mixed gas of methanol and ammonia was fed from the position 30 cm above the feed openings for air. By controlling the composition of the gases to be fed to the reactor so that the molar ratio of oxygen/methanol would be 1.36 and that the molar ratio of ammonia/methanol would be 1.0, and by regulating the gas velocity to 55 cm/s, the reaction was carried out at a temperature of 430° C. under a pressure of 0.5 kg/cm²G. At this time, the contact time was 1.8 seconds, the height "H" of the feed openings for methanol was 25%, and the catalyst bed density at the height "H" was 430 kg/M³. The results of the reaction were as follows: at 3 hours after the initiation of the reaction, the yield of hydrocyanic acid was 84.4% and the conversion of methanol was 99.9%; and at 300 hours after the initiation of the reaction, the yield of hydrocyanic acid was 81.5% and the conversion of methanol was 99.2%. The yield of hydrocyanic acid was thus found to be lowered with time.

Example B3

The ammoxidation reaction of methanol was carried out in the same manner as in Comparative Example B3, except that a mixed gas of methanol, ammonia and steam was fed from the position 140 cm above the feed openings for air which were positioned at the lower part of the reactor and that the reaction temperature was changed to 435° C. The molar ratio of the steam to methanol was adjusted to 1.0. At this time, the contact time was 1.3 seconds, the height "H" of the feed openings for methanol was 117%, and the catalyst bed density at the height "H" was 190 kg/m³. The results of the reaction were as follows: at 3 hours after the initiation of the reaction, the yield of hydrocyanic acid was 88.2% and the conversion of methanol was 99.7%; at 300 hours after the initiation of the reaction, the yield of hydrocyanic acid was 88.0% and the conversion of methanol was 99.3%; and at 900 hours after the initiation of the reaction, the yield of hydrocyanic acid was 88.0% and the conversion of methanol was 99.0%. The yield of hydrocyanic acid in Example B2 was higher than that in Comparative Example B3, and was maintained at a constant value for many hours. Thus, excellent results were obtained from the reaction, and, at the same time, the stabilization of the catalytic activity was attained.

Examples B4 and B5

454 g of Catalyst 3 (Example B4) or Catalyst 4 (Example B5) was packed in the same reactor as that used in Comparative Example B2 (the height of the stationary catalyst bed: 35 cm). Air was fed from the lower part of this reactor, while a mixed gas of methanol and ammonia was fed from the position 30 cm above the feed openings for air, and water vapor was fed from the position 5 cm above the same. By controlling the composition of the gases to be fed to the reactor so that the molar ratio of oxygen/methanol would be 1.36, that the molar ratio of ammonia/methanol would be 1.0 and that the molar ratio of steam/methanol would be 1.0, and by regulating the gas velocity to 15 cm/s, the reaction was carried out at a temperature of 440° C. under a pressure of 0.5 kg/cm²G. At this time, the contact time was 1.5 seconds, the height "H" of the feed openings for methanol was 86%, and the catalyst bed density at the height "H" was 240 kg/m³. The results of the reaction were as follows.

|  | After 1 hour | | After 20 hours | |
| --- | --- | --- | --- | --- |
|  | Yield of Hydrocyanic Acid (%) | Conversion of Methanol (%) | Yield of Hydrocyanic Acid (%) | Conversion of Methanol (%) |
| Example 4 | 86.0 | 98.5 | 86.2 | 98.7 |
| Example 5 | 85.5 | 99.0 | 85.2 | 98.9 |

What is claimed is:

1. In an ammoxidation method in a fluidized-bed reactor wherein a starting material to be ammoxidized is ammoxidized by means of vapor-phase catalytic fluidized-bed reaction, the improvement which comprises carrying out the reaction in a fluidized-bed reactor to which an oxygen-containing gas is fed through feed openings provided at the lower part thereof, and a starting material to be ammoxidized is fed through feed openings provided above the feed openings for the oxygen-containing gas, the distance between the feed openings for the oxygen-containing gas and those for the starting material being from 30 to 250% of the height, within the reactor, of a solid matter used to form the fluidized bed, as measured in a static state, so as to form such a fluidized bed that the density of the fluidized solid matter at the feed openings for the starting material to be ammoxidized is in the range of 50 to 300 kg/m³ and that the gas velocity is 1 m/s or lower.

2. The ammoxidation method in a fluidized-bed reactor according to claim 1, wherein the starting material to be ammoxidized is methanol, propylene or isobutylene.

3. The ammoxidation method in a fluidized-bed reactor according to claim 1, wherein the fluidized solid matter comprises a catalyst containing iron, antimony, and at least one element selected from the group consisting of boron, magnesium, phosphorus, potassium, titanium, vanadium, chromium, manganese, cobalt, nickel, copper, zinc, molybdenum, tin, tellurium, tungsten and bismuth.

4. In a method of ammoxidizing methanol wherein the vapor-phase catalytic ammoxidation of methanol is carried out in a fluidized-bed reactor under the conditions set forth in claim 1 to obtain hydrocyanic acid, the improvement which comprises carrying out the reaction by using, as a catalyst, a metallic oxide containing at least one element selected from the group consisting of iron, antimony, phosphorus and copper, and at least one element selected from the group consisting of vanadium, manganese, molybdenum, tungsten and bismuth, by feeding, to the catalyst bed, an oxygen-containing gas through feed openings provided at the lower part of the reactor, and methanol and ammonia as a gas which contains steam through feed openings provided above the feed openings for the oxygen-containing gas, or by feeding all of or a part of the steam to the catalyst bed through feed openings provided below the feed openings for methanol and ammonia, with the molar ratio of steam to methanol of 0.1 to 3.

5. The method of ammoxidizing methanol according to claim 4, wherein the proportion of the oxygen in the gases to be fed to the reactor is such that the molar ratio of oxygen to methanol is less than 1.6.

6. The method of ammoxidizing methanol according to claim 4, wherein the catalyst is a metallic oxide composition containing iron, antimony, phosphorus and vanadium.

7. The method of ammoxidizing methanol according to claim 5, wherein the vanadium content of the metallic oxide composition containing iron, antimony, phosphorus and vanadium is at least 0.6 for 10 of iron when expressed in an atomic ratio.

8. The method for ammoxidizing methanol according to claim 4, wherein the catalyst contains iron antimonate as a crystalline phase.

9. The method for ammoxidizing methanol according to claim 4, wherein the oxygen-containing gas is fed to the catalyst bed from openings provided at the lower part of the reactor, the methanol and ammonia are fed to the catalyst bed from openings provided above the openings for the oxygen-containing gas, the distance between the openings for the oxygen-containing gas and those for methanol and ammonia being from 30 to 250% of the height of the catalyst bed in a static state, and the catalyst bed density at the openings for methanol and ammonia is from 50 to 300 kg/m3.

10. In a method of ammoxidizing methanol wherein the vapor-phase catalytic ammoxidation of methanol is carried out in a fluidized-bed reactor under the conditions set forth in claim 1 to obtain hydrocyanic acid, the improvement which comprises carrying out the reaction by using, as a catalyst, a metallic oxide containing at least one element selected from the group consisting of iron, antimony, phosphorus and copper, and at least one element selected from the group consisting of vanadium, manganese, molybdenum, tungsten and bismuth, by feeding, to the catalyst bed, an oxygen-containing gas through feed openings provided at the lower part of the reactor, and methanol and ammonia as a gas which contains steam through feed openings provided above the feed openings for the oxygen-containing gas, or by feeding all of or a part of the steam to the catalyst bed through feed openings provided below the feed openings for methanol and ammonia, with the molar ratio of steam to methanol of 0.1 to 3, wherein the catalyst is represented by the following empirical formula:

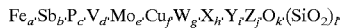

$Fe_a Sb_b P_c V_d Mo_e Cu_f W_g X_h Y_i Z_j O_k (SiO_2)_l$ wherein Fe, Sb, P, V, Mo, Cu and W represent iron, antimony, phosphorus, vanadium, molybdenum, copper and tungsten, respectively; X represents at least one element selected from the group consisting of Mg, Zn, La, Ce, Al, Cr, Mn, Co, Ni, Bi, U and Sn; Y represents at least one element selected from the group consisting of B and Te; Z represents at least one element selected from the group consisting of Li, Na, K, Rb, Cs, Ca and Ba; and the indexes a', b', c', d', e', f', g', h', i', j', k' and l' represent an atomic composition, where, when a' is 10, b' is from 12 to 30, c' is from 1 to 30, provided that b'/c' is larger than 1.5, d' is from 0.6 to 3, e' is from 0 to 0.3, f' is from 0 to 5, g' is from 0 to 3, h' is from 0 to 6, i' is from 0 to 5, j' is from 0 to 3, k' is a number corresponding to the oxide produced when the above components are combined, and l' is from 0 to 200.

11. The method for ammoxidizing methanol according to claim 10, wherein X represents at least one element selected from the group consisting of Mg, Zn, Al, Mn, Co and Ni.

12. The method for ammoxidizing methanol according to claim 10, wherein b' is from 15 to 27.

13. The method for ammoxidizing methanol according to claim 10, wherein c' is from 3 to 20.

14. The method for ammoxidizing methanol according to claim 10, wherein c' is from 5 to 15.

15. The method for ammoxidizing methanol according to claim 10, wherein d' is from 0.8 to 2.8.

16. The method for ammoxidizing methanol according to claim 10, wherein d' is from 1 to 2.5.

17. In an ammoxidation method in a fluidized-bed reactor wherein a starting material to be ammoxidized is ammoxidized by means of vapor-phase catalytic fluidized-bed reaction, the improvement which comprises carrying out the reaction in a fluidized-bed reactor to which an oxygen-containing gas is fed through feed openings provided at the lower part thereof, and a starting material to be ammoxidized is fed through feed openings provided above the feed openings for the oxygen-containing gas, the distance between the feed openings for the oxygen-containing gas and those for the starting material being from 30 to 250% of the height, within the reactor, of a solid matter used to form the fluidized bed, as measured in a static state, so as to form such a fluidized bed that the density of the fluidized solid matter at the feed openings for the starting material to be ammoxidized is in the range of 50 to 300 kg/m³ and that the gas velocity is 1 m/s or lower, wherein the catalyst is represented by the following empirical formula:

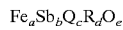

$Fe_a Sb_b Q_c R_d O_e$ wherein Q represents at least one element selected from the group consisting of V, Co, Ni, Cu, Mo, W and Bi; R represents at least one element selected from the group consisting of B, P, K, Zn and Te; and the indexes a, b, c, d and e represent an atomic ratio, where, when a is 1, b, c and d are $0.05 \leq b \leq 10$, $0.001 \leq c \leq 10$, and $0 \leq d \leq 5$, and e represents the number of oxygen atoms corresponding to the oxide produced when the above components are combined.

* * * * *